United States Patent [19]

Okabe

[11] Patent Number: 5,300,705
[45] Date of Patent: Apr. 5, 1994

[54] PROCESS FOR THE PREPARATION OF 1α,25,26-TRIHYDROXY-22-ENE-CHOLECAL-CIFEROL

[75] Inventor: Masami Okabe, Nutley, N.J.

[73] Assignee: Hoffmann-La Roche Inc., Nutley, N.J.

[21] Appl. No.: 32,905

[22] Filed: Mar. 18, 1993

[51] Int. Cl.$^5$ .................... C09J 9/00; C07C 85/11; C07C 35/08; C07C 401/00

[52] U.S. Cl. .................... 568/828; 568/832; 549/454; 549/341; 556/431; 556/443

[58] Field of Search .............. 568/833, 828, 832, 822, 568/700; 549/454, 341; 556/431, 443

[56] References Cited

U.S. PATENT DOCUMENTS

| | | | |
|---|---|---|---|
| 4,755,329 | 7/1988 | DeLuca et al. | 568/828 X |
| 5,110,958 | 5/1992 | Baggiolini et al. | 549/454 |
| 5,120,722 | 6/1992 | Baggiolini et al. | 514/167 |
| 5,225,579 | 7/1993 | Tahara | 568/828 X |

OTHER PUBLICATIONS

Tetrahedron Lett. 1988, 29, 227–230.
J. Org. Chem. 1988, 53, 3450–3457.
Tetrahedron Lett. 1984, 25, 3347–3350.
J. Org. Chem 1982, 47, 4770–4772.
Tetrahedron Lett. 1992, 33, 2937–2940.
Calverley, M. J. Tetrahedron 1987, 43, 4609–4619.
J. Org. Chem. 1993, 58, 1496–1500.
J. Am. Chem. Soc. 1982, 104, 4724–4725.
J. Org. Chem. 1992, 57, 33–39.
J. Org. Chem. 1978, 43, 790–792.
Tetrahedron Lett. 1992, 33, 3741–3744.

Primary Examiner—Arthur C. Prescott
Attorney, Agent, or Firm—George M. Gould; George W. Johnston; Ellen Ciambrone Coletti

[57] ABSTRACT

A process for preparing 1α,25(R),26-trihydroxy-22E-ene-cholecalciferol and 1α,25(S),26-trihydroxy-22E-ene-cholecalciferol.

12 Claims, No Drawings

PROCESS FOR THE PREPARATION OF 1α,25,26-TRIHYDROXY-22-ENE-CHOLECALCIFEROL

BACKGROUND OF THE INVENTION

1α,25(R),26-trihydroxy-22-ene-cholecalciferol and 1α,25(S),26-trihydroxy-22-ene-cholecalciferol are known compounds useful in the treatment of leukemia. U.S. Pat. No. 5,110,958, filed May 5, 1992, and U.S. Pat. No. 5,120,722, filed Jun. 9, 1992.

The known methods of preparing 1α,25(R),26-trihydroxy-22-ene-cholecalciferol and 1α,25(S),26-trihydroxy-22-ene-cholecalciferol, include those set forth in U.S. Pat. Nos. 5,110,958 and 5,120,722.

BRIEF SUMMARY OF THE INVENTION

The invention relates to a process for the preparation of the compounds 1α,25(R),26-trihydroxy-22-ene-cholecalciferol and 1α,25(S),26-trihydroxy-22-ene-cholecalciferol, represented by the formula

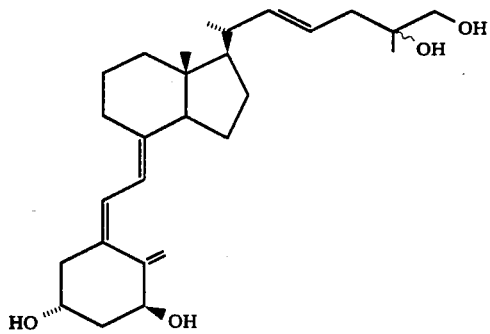

which process comprises, a) reacting a compound of formula II, Ph₃P=CHLi, with a specific epimer of the formula

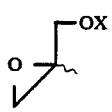

wherein X is an oxygen protecting group, to form a specific epimer of the formula

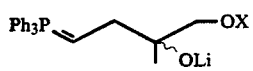

wherein X is as described above, b) reacting the specific epimer of formula IV with a compound of the formula

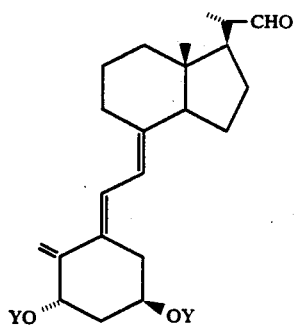

wherein Y is a silyl containing oxygen protecting group to form the corresponding specific epimer of the formula

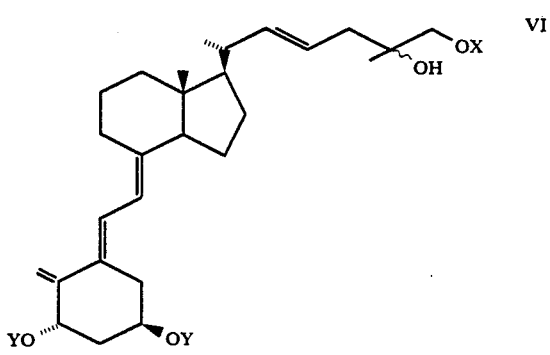

wherein X and Y are as previously described, c) reacting the specific epimer of formula VI to form the corresponding specific epimer of the formula

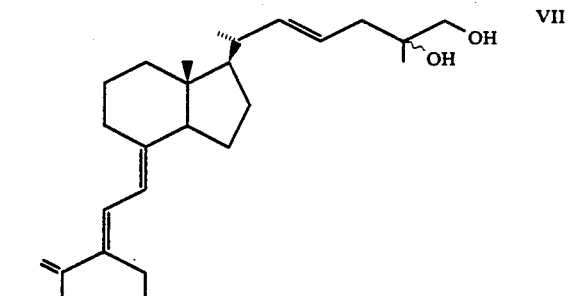

and d) isomerizing the specific epimer of formula VI to form the corresponding specific epimer of formula I.

DETAILED DESCRIPTION OF THE INVENTION

In the formulas represented herein, when substituents are illustrated as joined to the nucleus by a solid line (◂), it indicates that the substituent is above the plane of the molecule, a broken line (ıııı), indicates that the substituent is below the plane of the molecule, and a wavy line (∼) indicates that the substituent is either above the plane of the molecule or below the plane of the molecule.

It is understood that while the C-25 epimers are prepared and discussed individually, mixtures of the C-25 epimers are also within the scope of the invention.

As used herein, the term "oxygen protecting group" denotes ether or silyl ether, such as tetrahydropyranyl ether or

wherein $R^1$, $R^2$, and $R^3$ are independently alkyl or phenyl, preferably a trialkylsilyl group.

The term "alkyl", alone or in combination, denotes a straight-chain or branched chain alkyl group containing 1 to 10, preferably 1 to 6, carbon atoms.

The invention relates to a process for the preparation of the compounds 1α,25(R),26-trihydroxy-22-ene-cholecalciferol and 1α,25(S),26-trihydroxy-22-ene-cholecalciferol, represented by the formula

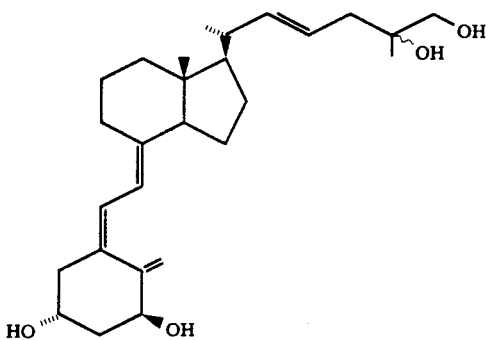

I which process comprises, a) reacting a compound of formula II, $Ph_3P=CHLi$, with a specific epimer of the formula

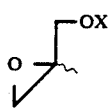

III wherein X is an oxygen protecting group, preferably a trialkylsilyl group, to form the corresponding specific epimer of the formula

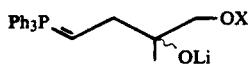

IV wherein X is as described above, b) reacting the specific epimer of formula IV with a compound of the formula

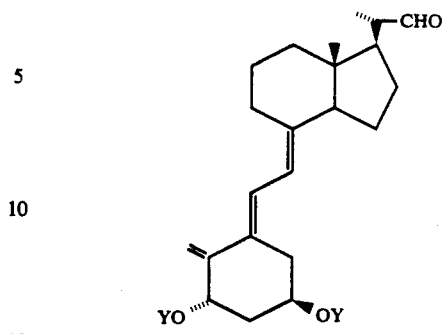

V wherein Y is an oxygen protecting group, preferably trialkyl silyl group, to form the corresponding specific epimer of the formula

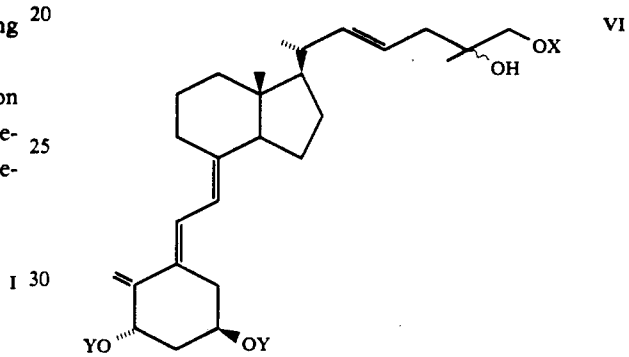

VI wherein X and Y are as described above, c) reacting a compound of formula VI to form the corresponding specific epimer of the formula

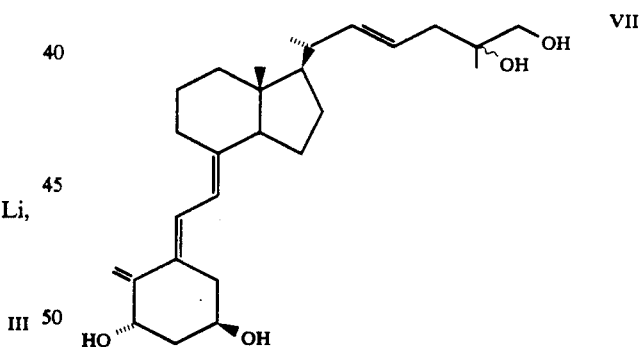

VII and d) isomerizing a compound of formula VII to form the corresponding specific epimer of formula I.

In accordance with the invention, a compound of the formula $[Ph_3P—CH_3]+Z-$, wherein Z is halogen other than fluorine, is treated with sec.butyllithium or tert.butyllithium in an aprotic organic solvent, preferably ether, to form a known compound of formula II, which is reacted with a specific epimer of formula III, a known compound or which can be prepared by known methods, to yield the corresponding specific epimer of formula IV. The reaction is carried out in an aprotic organic solvent, such as, for example, ether or tetrahydrofuran, preferably ether.

The specific epimer of formula IV is reacted with a compound of formula V, a known compound or which can be prepared by known methods, to form the corresponding specific epimer of formula VI. The reaction is carried out in an aprotic organic solvent, such as, for example, ether or tetrahydrofuran, preferably ether, at a temperature preferably in the range of −78° to 25° C.

The specific epimer of formula VI is treated with a fluoride salt, such as, for example, tetrabutylammonium fluoride in tetrahydrofuran to form the corresponding specific epimer of formula VII.

The specific epimer of formula VII is subjected to photo isomerization, preferably using 9-acetylanthracene as the catalyst in methanol and tert.butyl methyl ether to form a corresponding compound of formula I.

The examples which follow further illustrate the invention.

EXAMPLE 1

(1α,3β,5E,7E,22E,25R)-1,3-bis[[(1,1-Dimethylethyl)-dimethylsilyl]oxy]-26-[[dimethyl(1,1,2-trimethylpropyl)silyl]oxy]-9,10-secocholesta-5,7,10(19),22-tetraen-25-ol A 250-mL three-necked flask equipped with a magnetic stirrer, additional funnel, thermometer, and Ar-inlet tube was charged with 6.48 g (18.1 mmol) of methyltriphenylphosphonium bromide and 65 mL of anhydrous ether (distilled from sodium/benzophenone immediately prior to use). After the suspension was cooled to −30° C., 30.9 mL (40.2 mmol) of a 1.3M sec.butyllithium in cyclohexane was added dropwise over 5 minutes. The cold-bath was removed and the mixture was stirred at room temperature for 4 hours. After the resulting orange suspension was cooled to 5° C., 7.11 g (30.8 mmol) of (R)-dimethyl[(2-methyloxiranyl)methoxy] (1,1,2-trimethylpropyl)silane was added. After 20 minutes, the cold-bath was removed and the mixture was stirred at room temperature overnight (about 19 hr). The yellow suspension was then cooled to −70° C., and 7.43 g (12.9 mmol) of (1α,3β, 5E,7E,20S)-1,3-bis[[(1,1-dimethylethyl)dimethylsilyl]oxy]-9,10-secopregna-5,7,10(19)-triene-20-carboxaldehyde was added. The mixture was stirred at −70° C. for 1 hour and then slowly warmed up to room temperature over a period of 1.5 hours. The reaction mixture was cooled again to 5° C. and quenched by the addition of 1.48 mL (25.9 mmol) of acetic acid followed by cautious addition of 100 mL of water. The mixture was extracted with 100 mL then 50 mL of ether. The combined organic layers were dried over $Na_2SO_4$, and concentrated. The residue was partitioned between 100 mL of hexane and 100 mL of 95% methanol. The hexane layer was washed with 50 mL of 95% methanol. The combined methanol layers were extracted with 50 mL of hexane. The hexane layers were combined, dried over $Na_2SO_4$, and concentrated. The residue was suspended in 50 mL of methanol, and the mixture was cooled with an ice-water bath to solidify the product. The resulting suspension was diluted with 50 mL of 95% methanol and stirred at 0° C. for 1.5 hr prior to filtration. The solid was washed with 50 mL of cold 95% methanol and dried under high vacuum overnight to give 8.2 g of crude title compound. This was suspended in 50 mL of methanol, and the mixture was stirred at room temperature for 1 hour. After dilution with 50 mL of 95% methanol, the mixture was stirred at 0° C. for 1.5 hours. The precipitate was then filtered, washed with 20 mL of 95% methanol, and dried overnight under high vacuum to give 7.38 g (71.0%) of (1α,3β,5E,7E,22E,25R)-1,3-bis[[(1,1-dimethylethyl)dimethylsilyl]oxy]-26-[[dimethyl(1,1,2-trimethylpropyl)silyl]oxy]-9,10-secocholesta-5,7,10(19),22-tetraen-25-ol as a white solid: mp 82°-86° C. Anal. Calcd. for $C_{47}H_{88}O_4Si_3$: C, 70.44; H, 11.07; Si, 10.51. Found: C, 70.08; H, 11.05; Si, 10.24.

EXAMPLE 2

(1α,3β,5E,7E,22E,25R)-9,10-Secocholesta-5,7,10(19),22-tetraene-1,3,25,26-tetrol

A 100-mL flask equipped with a magnetic stirrer and an Ar-inlet tube was charged with 7.38 g (9.2 mmol) of (1α,3β,5E,7E,22E,25R)-1,3-bis[[(1,1-dimethylethyl)-dimethylsilyl]oxy]-26-[[dimethyl(1,1,2-trimethylpropyl)silyl]oxy]-9,10-secocholesta-5,7,10(19),22-tetraen-25-ol and 92 mL (92 mmol) of a 1M tetrabutylammonium fluoride in tetrahydrofuran. The solution was stirred at 30° C. for 24 hours, and then poured into a stirred mixture of 300 mL of water and 100 mL of hexane. The resulting suspension was stirred at room temperature for 2.5 hours. The precipitate was then filtered and washed with 2×50 mL of water and then with 2×50 mL of hexane. After drying under high vacuum overnight, the solid was dissolved in 20 mL of warm methanol, and then diluted with 15 mL of water. After brief warming of the suspension, the mixture was stored in a refrigerator overnight. The precipitate was filtered and washed with 20 mL of cold 50% methanol. After drying under high vacuum for 40 hours, 3.23 g (81.5%) of (1α, 3β,5E,7E, 22E,25R)-9,10-secocholesta-5,7,10(19),22-tetraene-1,3,25,26-tetrol was obtained as a white solid: mp 163°-166° C. Anal. Calcd. for $C_{27}H_{42}O_4$: C, 75.31; H, 9.83; Found: C, 75.06; H, 9.73.

EXAMPLE 3

1α,25R,26-Trihydroxy-22E-ene-cholecalciferol

A 2 L photochemical reaction flask equipped with a Pyrex immersion well, thermometer, Ar-inlet tube, and mechanical stirrer was charged with 3.20 g (7.43 mmol) of (1α,3β,5E,7E,22E,25R)-9,10-secocholesta-5,7,10(19),22-tetraene-1,3,25,26-tetrol, 64 mg of 9-acetylanthracene, 1.2 L of methanol and 0.5 L of tert-.butyl methyl ether. The solution was cooled to −20° C. and irradiated with a 450 W medium pressure mercury lamp through a uranium glass filter for 3 hours. The solution was concentrated at room temperature to give a white solid, and it was suspended in 100 mL of ethyl acetate. After stirring at room temperature for 1 hour, the suspension was diluted with 25 mL of hexane, and stored in a refrigerator overnight. The solid was filtered and washed with 70 mL of ethyl acetate-hexane (3:1). 3.11 g of the crude product thus obtained was dissolved in 62 mL of methanol at reflux. After cooling to about 40° C., the solution was diluted with 31 mL of water, and stirred at room temperature overnight prior to filtration. The solid was washed with 30 mL of 50% methanol and dried under high vacuum for 30 hours to give 2.85 g (89.1%) of 1α,25R,26-trihydroxy-22E-ene-cholecalciferol as a white solid: mp 176°-178° C. Anal. Calcd. for $C_{27}H_{42}O_4$: C, 75.31; H, 9.83; Found: C, 75.06; H, 9.90.

I claim:

1. A compound of the formula

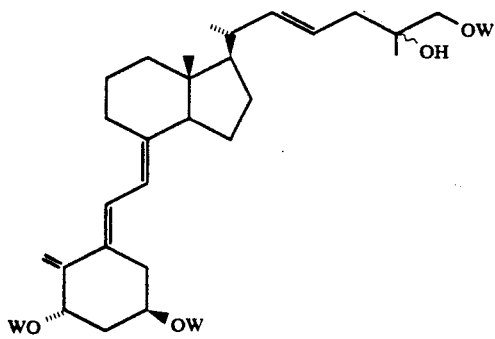

wherein W is hydrogen or the same or different oxygen protecting group.

2. The compound of claim 1, wherein W is selected from the group consisting of tert.butyldimethylsilyl and thexyldimethylsilyl groups.

3. The compound of claim 1, (1α,3β,5E,7E,22E,25R)-9,10-secocholesta-5,7,10(19),22-tetraene-1,3,25,26-tetrol.

4. The compound of claim 1, (1α,3β,5E,7E,22E,25S)-9,10-secocholesta-5,7,10(19),22-tetraene-1,3,25,26-tetrol.

5. The compound of claim 2, (1α,3β,5E,7E,22E,25R)-1,3-bis[[(1,1-dimethyl)dimethylsilyl]oxy]-26-[[dimethyl(1,1,2-trimethylpropyl)silyl]oxy]-9,10-secocholesta-5,7,10(19),22-tetraen-25-ol.

6. The compound of claim 2, (1α,3β,5E,7E,22E,25S)-1,3-bis[[(1,1-dimethyl)dimethylsilyl]oxy]-26-[[dimethyl(1,1,2-trimethylpropyl)silyl]oxy]-9,10-secocholesta-5,7,10(19),22-tetraen-25-ol.

7. A compound of the formula

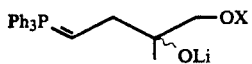  IV wherein X is an oxygen protecting group.

8. The compound of claim 7, wherein X is

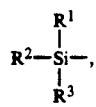

$R^1$, $R^2$ and $R^3$ are independently $C_1$–$C_6$ alkyl or phenyl.

9. The compound of claim 8, wherein X is a thexyldimethylsilyl group.

10. A process for preparing a specific epimer of the formula

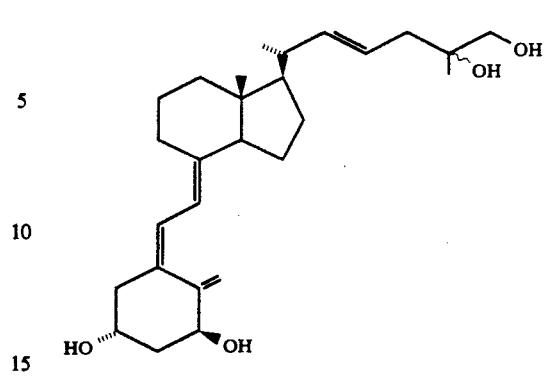  I comprising a) reacting a compound of the formula $Ph_3P=CHLi$, with a specific epimer of the formula

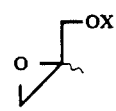  III wherein X is an oxygen protecting group to form the specific epimer of the formula

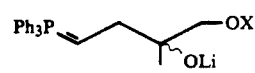  IV wherein X is as described above b) reacting the specific epimer of formula IV with a compound of the formula

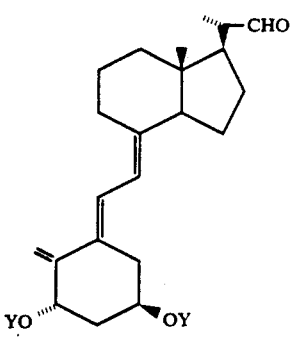  V wherein Y is a silyl containing oxygen protecting group, to form a specific epimer of the formula

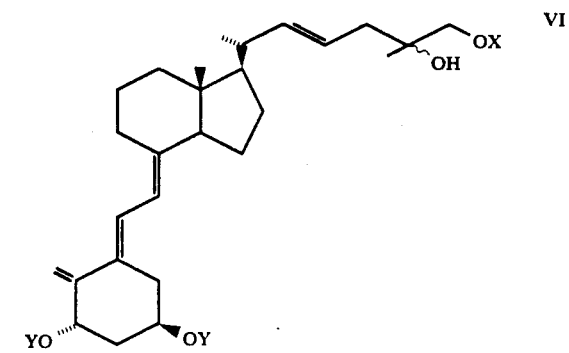  VI wherein X and Y are as described above c) reacting the specific epimer of formula IV to form a specific epimer of the formula

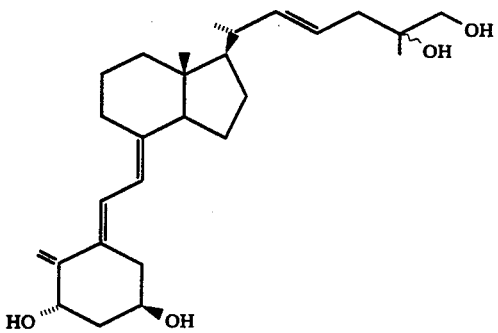

VII d) isomerizing the specific epimer of formula VII to form a specific epimer of formula I.

11. The process of claim 10, wherein X is tetrahydropyranyl ether or

wherein $R^4$, $R^5$, $R^6$ are independently alkyl or phenyl.

12. A process for preparing a compound of the formula

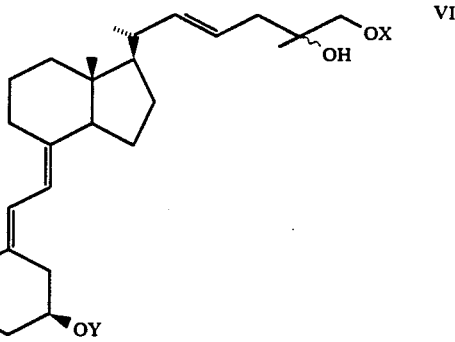

VI wherein X and Y are the same or different silyl containing oxygen protecting group, comprising reacting a compound of the formula

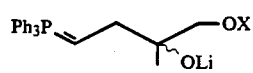

IV wherein X is a silyl containing oxygen protecting group, with a compound of the formula

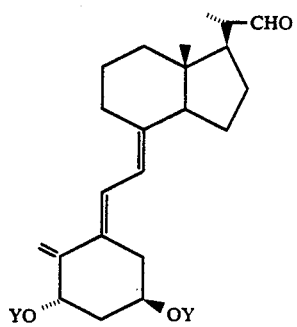

V wherein Y is as described above.

* * * * *